United States Patent [19]

Ryan et al.

[11] Patent Number: 4,544,545
[45] Date of Patent: Oct. 1, 1985

[54] LIPOSOMES CONTAINING MODIFIED CHOLESTEROL FOR ORGAN TARGETING

[75] Inventors: Patrick J. Ryan, Worcester; Michael A. Davis, Westwood; Donald L. Melchior, Framingham, all of Mass.

[73] Assignee: Trustees University of Massachusetts, Amherst, Mass.

[21] Appl. No.: 505,696

[22] Filed: Jun. 20, 1983

[51] Int. Cl.⁴ .................... A61K 49/00; A61K 43/00; A61K 39/00
[52] U.S. Cl. ........................................ 424/1.1; 424/9; 424/7.1; 424/16; 424/85; 424/88; 424/94; 252/315.3
[58] Field of Search ...................... 424/1.1, 9, 16, 7.1, 424/85, 88, 94; 252/315.3

[56] References Cited

U.S. PATENT DOCUMENTS 3,932,657  1/1976  Rahman .............................. 424/1.1
4,310,505  1/1982  Baldeschwieler et al. .......... 424/1.1
4,343,895  8/1982  Sugaar ................................. 435/6

OTHER PUBLICATIONS

Ryan et al, Biochim. Biophys. Acta, 756, (1983), 106–110.
Stoffel et al, Hoppe-Seyler's Z. Physiol. Chem. 357, (1976), 21–33.

Primary Examiner—Christine M. Nucker
Attorney, Agent, or Firm—Paul J. Cook

[57] ABSTRACT

Phospholipid liposomes are provided having an outer layer including a cholesterol derivative such as a cholesterol ester and an aqueous medium confined by the layer which includes a tracer agent, a cytoxic agent or a therapeutic agent. The liposomes are adapted for specific organ targeting.

12 Claims, No Drawings

4,544,545

LIPOSOMES CONTAINING MODIFIED CHOLESTEROL FOR ORGAN TARGETING

BACKGROUND OF THE INVENTION

The present invention relates to the preparation of liposomes adapted for specific organ targeting and to the liposomes so prepared.

Liposomes are synthetic lipid vesicles whose lipid bilayers serve as a model of biomembranes. Liposomes can be prepared by a various of techniques to yield vesicles of varying size and lamellar structure. They usually have a maximum diameter on the order of 100,000 Å and most often have a diameter between 110 to 10,000 Å, bounded by a wall formed by at least one bimolecular layer (having a thickness on the order 100 Å) of a compound of the general formula XY, where X is a hydrophilic polar group and Y is a hydrophobic non-polar group, the globules containing an aqueous liquid, for example and aqueous solution of at least one biologically active substance, and existing generally in the form of a colloidal dispersion in an aqueous medium such as an aqueous saline solution, in particular a 0.9% by weight sodium chloride solution.

The preparation of liposomes provides a method of encapsulation which is most practical and effective for aqueous materials as well as hydrophobic and amphipathic material and which is particularly useful for administration of biologically active substances, particularly medicaments, into living organisms, while avoiding the destruction or inactivation of the substance in the organism, for example by the action of gastric or intestinal juices, before the substances reach the site where they are required to act.

Central to this interest is an altered biodistribution of the agent to various organs, tissues or inflammatory sites.

Targeting of encapsulated material in liposomes has the advantage of increased specific activity of the agent to the specific target site, lowered exposure of other areas to the agent thereby decreasing effective toxicity of the agent and altered time course of agent delivery. Loaded vesicles, therefore, hold promise of therapeutic and diagnostic use in cancer patients. Multilamellar as well as unilamellar lipid vesicles loaded with a radiopaque agent have been shown to enhance hepatic and splenic imaging of the rat by X-ray computed tomography.

By selection of the compound of formula XY used to form the wall of the liposomes, it is possible to produce liposomes having walls which resist the degradation by various physiological processes.

Typical processes for the preparation of liposomes include placing a lipid in contact with an aqueous liquid that is desired to be encapsulate and then warming the heterogeneous mixture thus obtained at a temperature slightly above ambient temperature and then submitting the mixture to vigorous agitation following ultrasonic vibration.

Another process consists of dissolving a compound of formula XY (where X and Y are defined above), for example a lipid, in a volatile solvent, forming a film of the compound on the walls of a receptacle by evaporating the solvent from the solution thus obtained, introducing in the same receptacle the liquid which is desired to encapsulate in the liposomes, and finally submitting the liquid in the receptacle to the action of ultrasonic vibrations.

It would be highly desirable to provide a means for rendering liposomes more selective for a particular organ in order to improve their selectivity to deliver biologically active agents or contrast agents which can be detected by conventional scanning apparatus.

SUMMARY OF THE INVENTION

The present invention is based upon the discovery that liposomes formed with chemically modified cholesterol can be rendered selective for targeting specific organs by adjusting the type of chemical modification employed. The liposomes are formed by conventional means but with the addition of the chemically modified cholesterol to the liposome-forming composition. An aqueous composition containing the diagnostic or therapeutic agent is admixed with a carrier liquid composition which is insoluble or only slightly soluble in water. The resultant mixture may be subjected to vigorous agitation such as ultrasonic agitation or prepared by emulsifying aqueous droplets containing the desired material to be encapsulated in organic solvent, forming a gel by evaporation of solvent and addition of an aqueous phase to form the liposomes that can be unilamellar or multilamellar, the interiors of which are filled with the aqueous composition. Similarly natural membranes may be used as a target vehicles containing various agents by introducing cholesterol derivatives into their membranes. The cholesterol is chemically modified with a ligand designed to be recognized by a particular organ or cell type such as a long chain fatty acid, an amino acid, an oligosaccharide, a horomone, an amino acid derivative, a protein, glycoprotein, or modified protein, or the like. The resultant liposome is suitable for being targeted to a specific organ or cell type.

DESCRIPTION OF SPECIFIC EMBODIMENTS

In accordance with this invention, liposomes are provided which contain a tracer material, a cytotoxic agent or a therapeutic agent. The liposomes of this invention are characterized by the inclusion in the monolayer or bilayer a chemically modified cholesterol which is modified so that the liposome is rendered more specific for rapid and preferential accumulation in vivo to a specific desired organ. The liposomes can be unilamellar or multilamellar and can be formed from any lipid material conventionally utilized to form liposomes. Representative suitable lipid materials that can be utilized to form liposomes include distearoyl phosphatidylcholine and/or L-α-dipalmitoyl phosphatidylcholine or similar lipid substances or naturally occurring cells such as red blood cells. The walls of the liposomes can also be formed from soybean phospholipid, egg yolk lecithin and L-60 -dimyristoyl phosphatidylcholine. The liposomes may be prepared by simple sonication from liquid suspension, hydration of crystallized lipids or any other conventional procedure well known in the art. Generally, the liposomes have a size range of between about 0.001 and about 10 microns.

\* The modified cholesterol of the invention must be modified at the hydroxyl group positioned at the 3 position on the cholesterol molecule because this hydroxyl group is oriented on the outside surface of the lipid bilayer.

For purposes of this invention, cholesterol is modified with a ligand such as is set forth above. The following table lists the human organs, the ligands are characterized by high uptake by the organ in accordance with this invention and the cholesterol derivatives that would be utilized.

TABLE 1

| Organ | Ligand | Cholesterol Derivative |
|---|---|---|
| Heart | Fatty acids | Chol-butyrate, chol-hexanate |
| Prostrate | Cadaverine | N—cadaverinyl chol-carbamate |
| Liver | Desialated glyco-protein | Carbamate or ester linkage between chol and ligand |
| Pancreas | Phenylalanine | chol-phenylacetate |
| Pancreas | Procainamide | N—procainamidyl-chol-carbamate |
| Adrenal | Cholesterol | Cholesteric cholesterate |

The modified cholesterol is added to the lipids when forming the liposomes and is generally added at a concentration of between about 0.1 to 5 mole percent of total bilayer lipids preferably between about 1.0 and about 3.0 mole percent.

The aqueous portion of the liposome contains the tracer material, cytotoxic agent or therapeutic agent which is to be delivered to the desired organ by the liposome. Representative suitable agents which can be delivered by the liposomes of this invention include radioactive tracers such as iodine-131, iodine-123, iodine-126, iodine-133, bromine-17, indium-111, indium 113 m, gallium-67, gallium-68, ruthenium-95, ruthenium-97, ruthenium-103, ruthenium-105, mercury-107, mercury-203, rhenium-99 m, rhenium-105, rhenium-101, tellurium-121 m, technetium-99 m or the like which are useful in radionuclide scintigraphy; fluorescent agents such as fluoroscein, tetrachycline; radiographic contrast agents such as diatrizoate, metrizamide, iothalamate or the like which are useful in fluoroscopy, plain film X-ray, angiography, digital subtraction angiography and computed tomography; diamagnetic and paramagnetic substances such as perfluorohydrocarbons, nitroxide free radicals, phosphates, magnesium, gadolinium or the like, which are useful in nuclear magnetic resonance imaging or gaseous agents or gaseous percursors auch as carbon dioxide, helium, argon, bicarbonates, aminomalonate carbonates, xenon or the like which are useful in ultra-songraphic applications. Representative suitable therapeutic or cytotoxic agents include anti-cancer agents, anti-infection agents, anti-inflammatory agents, enzymes or the like such as methotrexate, ricin-A chain, 5 FU, Adriamycin, 6 MP, Azaserine, asparaginase, dexamethasone, prostaglandins, ara-A- or the like. Other agents which can be incorporated into the liposomes of this invention include genetic material which is useful in treating inborn errors of metabolism such as those used in glycogen storage diseases, lipidoses or the like.

After formation of the liposomes, they can be utilized be being suspended in a physiologically acceptable liquid such as saline and administered parenterally, orally, intramuscularly, subcutaneously, intraperitoneally, rectally, intralymphoatically and intrathecally.

The following example illustrates the present invention and are not intended to limit the same.

EXAMPLE 1

A quanity of 126 mg of egg lecithin (egg phosphatidyl choline), 27 mg of cholesterol and an amount of cholesterol phenylacetate (30 mg) are mixed in 9 ml diethyl ether. 3 ml of diatrizoate sodium is added to the flask and the mixtures sonicated until a homogeneous suspension is obtained. Diethyl ether is removed by rotary evaporation under a water aspirator. Saline is added to the residue to complete lipsome formation. Unencapsulated diatrizoate is removed by centrifugation. Resuspension of the pelletized liposomes in saline yields the final material; injection of a portion of this material (20%) into a rat is followed by significant contrast enhancement of the pancreas, liver and spleen on subsequent computed tomographic scans of the rat.

We claim:

1. In a liposome formed by the incapsulation of an active agent by at least one lipid containing bilayer, the improvement comprising a ligand modified cholesterol compound in the lipid of said bilayer, said ligand being positioned at the 3 carbon position of said cholesterol, said ligand modified cholesterol compound rendering the liposome more specific for accumulation at a preselected organ in vivo.

2. The liposomes of claim 1 wherein said modified cholesterol is cholesterol butyrate.

3. The liposomes of claim 1 wherein said modified cholesterol is cholesterol phenylacetate.

4. The liposomes of any one of claims 1, 2 or 3 wherein said lipid bilayer includes a radioactive cation.

5. The liposomes of any one of claims 1, 2 or 3 wherein said lipid bilayer includes a fluorescent dye.

6. The liposomes of any one of claims 1, 2 or 3 wherein said lipid bilayer includes gaseous material.

7. The liposomes of any one of claims 1, 2 or 3 wherein said lipid bilayer includes a drug.

8. The liposomes of any one of claims 1, 2 or 3 wherein said lipid bilayer includes an enzyme.

9. The liposomes of any one of claims 1, 2 or 3 wherein said lipid bilayer includes metallic ions.

10. The liposomes of any one of claims 1, 2 or 3 wherein said lipid bilayer includes a magnetic compound.

11. The liposomes of any one of claims 1, 2 or 3 wherein said lipid bilayer includes genetic material.

12. The liposomes of any one of claims 1, 2 or 3 wherein said lipid bilayer includes an antigen or antibody.

* * * * *